(12) United States Patent
Axexandersen et al.

(10) Patent No.: US 6,939,339 B1
(45) Date of Patent: Sep. 6, 2005

(54) ACCESS MEMBER AND A SYSTEM FOR CATHETERIZATION OF THE URINARY BLADDER THROUGH AN ARTIFICIAL OR A NATURAL CANAL IN A USER, AND A METHOD OF REPLACING SUCH AN ACCESS MEMBER

(75) Inventors: Morten Bay Axexandersen, Alsgårde (DK); Suzanne Fis Benzon, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 354 days.

(21) Appl. No.: 10/019,465

(22) PCT Filed: Jul. 3, 2000

(86) PCT No.: PCT/DK00/00361

§ 371 (c)(1),
(2), (4) Date: Apr. 8, 2002

(87) PCT Pub. No.: WO01/02044

PCT Pub. Date: Jan. 11, 2001

(30) Foreign Application Priority Data

Jul. 2, 1999 (DK) .............................. 1999 00958

(51) Int. Cl.[7] ..................... A61M 27/00; A61M 25/00; A61M 5/00
(52) U.S. Cl. ..................... 604/544; 540/523; 540/172
(58) Field of Search ............................... 604/540, 541, 604/543–544, 171, 172, 523, 524

(56) References Cited

U.S. PATENT DOCUMENTS

| | | | |
|---|---|---|---|
| 3,854,483 A * | 12/1974 | Powers ...................... 604/172 |
| 3,881,199 A | 5/1975 | Treace ............................. 3/1 |
| 4,652,259 A | 3/1987 | O'Neil ........................ 604/54 |
| 4,684,369 A | 8/1987 | Wildemeersch ............. 604/272 |
| 4,710,169 A * | 12/1987 | Christopher ................ 604/104 |
| 5,417,666 A | 5/1995 | Coulter ....................... 604/172 |
| 5,704,353 A | 1/1998 | Kalb et al. .................. 128/634 |
| 5,792,114 A * | 8/1998 | Fiore ........................... 604/171 |
| 5,806,527 A | 9/1998 | Borodulin et al. .......... 128/885 |
| 5,910,128 A | 6/1999 | Quinn ......................... 604/93 |

FOREIGN PATENT DOCUMENTS

| | | |
|---|---|---|
| GB | 2 179 258 | 3/1987 |
| GB | 2 275 420 | 8/1994 |
| WO | 95/17873 | 7/1995 |

* cited by examiner

*Primary Examiner*—Larry I. Schwartz
*Assistant Examiner*—Linh Truong
(74) *Attorney, Agent, or Firm*—Jacobson Holman PLLC

(57) ABSTRACT

An access member for use in catheterization having an outer end and an inner end. The access member, which is adapted to extend from the outside of the body through a canal extending from the user's abdominal wall to the bladder and into the bladder, has at least one cavity extending substantially throughout the length of the access member. The walls of the access member are made from a flexible material such that the cavity is generally kept closed by the mutual contact of the walls while allowing for intermittent insertion of a catheter.

20 Claims, 2 Drawing Sheets

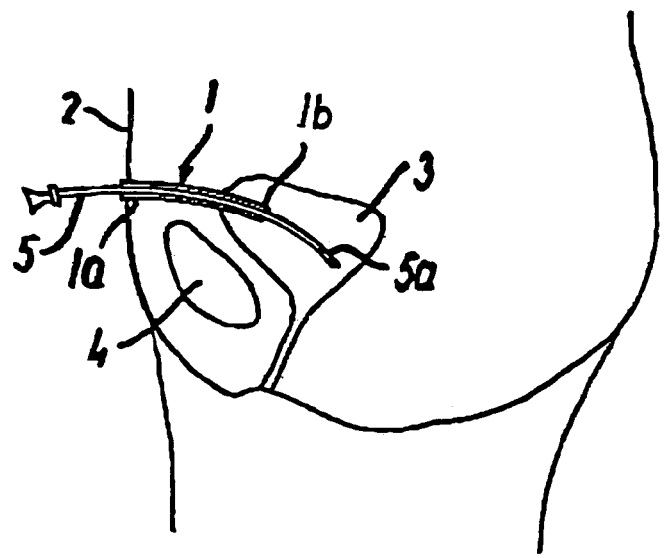
FIG.1
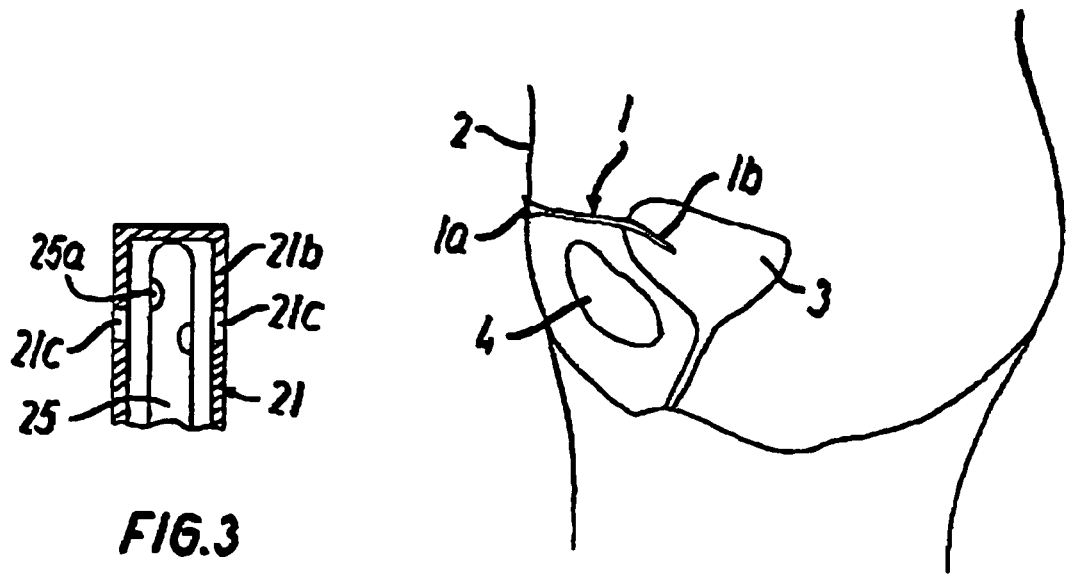
FIG.3
FIG.2

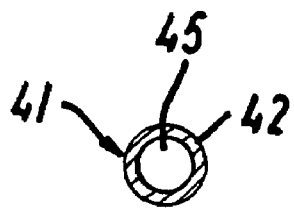
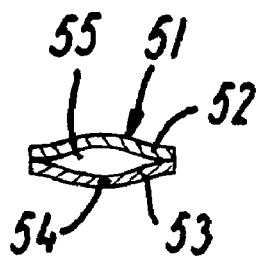
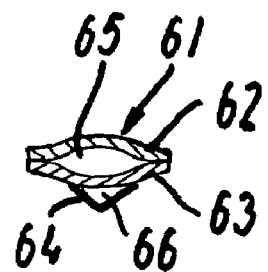
FIG. 4      FIG. 5      FIG. 6
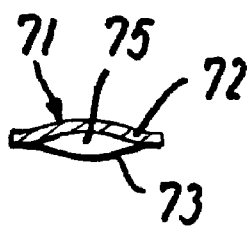
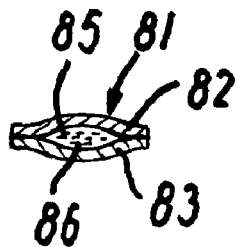
FIG. 7      FIG. 8
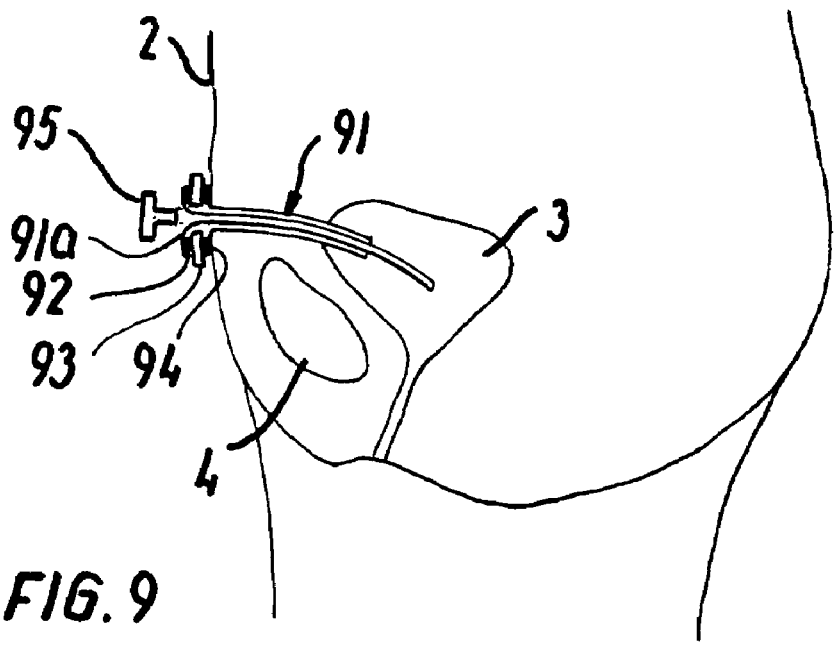
FIG. 9

ACCESS MEMBER AND A SYSTEM FOR CATHETERIZATION OF THE URINARY BLADDER THROUGH AN ARTIFICIAL OR A NATURAL CANAL IN A USER, AND A METHOD OF REPLACING SUCH AN ACCESS MEMBER

This is a nationalization of PCT/DK00/00361, filed Jul. 3, 2000 and published in English.

BACKGROUND OF THE INVENTION

The present invention relates to an access member and a system for catheterization of the urinary bladder through an artificial or a natural canal in a user. The invention furthermore relates to a method of replacing such an access member Catheterization may typically be necessary in the case of postoperative urine retention of newly operated patients in a hospital. Another typical use is with patients suffering from severe cases of urinary incontinence as for disabled individuals like para- or tetraplegics who frequently have no control permitting voluntary urination.

Traditionally, such catheterization is carried out by inserting a catheter through the urethra of the patient. The catheter may be left in place for permanent catheterization during several hours or days, which is typically the case in elderly and infirm patients, or be retracted after emptying of the bladder, ie. so-called intermittent catheterization (IC).

Access to the urinary bladder may likewise be desirable in order to introduce eg. pharmaceuticals into the bladder or in order to wash or rinse the bladder.

Intermittent urethral catheterization performed with intervals of eg. 3 to 6 hours reduces the risk of infection of urethra and the bladder significantly as compared to permanent catheterization and has for many users become increasingly common also in daily life situations outside the clinical environment of a hospital, whereby a significantly improved quality of life has been obtained for this group of patients.

However, intermittent catheterization requires a certain degree of dexterity and mobility which implies that self-catheterization is not always possible, especially in women where the urethral orifice may be difficult to locate.

During recent years, suprapubic catheterization (SPC) has been introduced as an alternative to urethral catheterization. In suprapubic catheterization, a canal is made from the surface skin of the abdominal wall of a user into the bladder under local or general anaesthetia and by means of a pointed hollow introducer or trocar. After penetration of the trocar into the bladder, a catheter is inserted through the canal thus provided, the inner end of said catheter being retained in the bladder by means of eg. an inflatable balloon abutting the inner wall of the bladder after retraction of the trocar. Although many of the disadvantages connected with urethral catheterization, such as eg. urethral cleavage and urethritis, may be overcome by this technique, infection risk is still high as suprapubic catheterization is typically performed as permanent catheterization due to the fact that the canal may close during replacement of the catheter. Furthermore, the fact that the end of the catheter protrudes well into the bladder when using a balloon, which is necessarily placed at a distance from the end in order to allow in-flow of urine, means that the bladder wall may be injured, the more so as the bladder wall often assumes an at least partially collapsed position in which it rests on the end of the catheter.

GB patent No. 2 275 420 discloses a system for suprapubic catheterization of the bladder permitting intermittent catheterization by means of an accessor or sealing member permanently lodged in the artificial canal. The accessor comprises an outer shell formed by two elongate leaves of a bendable plastics material which are hinged together along one edge and having flanges at one end for securing the accessor to the skin surface. A sealing means in the form of a balloon assembly keeps the canal formed in the accessor closed between emptyings but allows insertion of the catheter. Due to the size and material of the accessor, this system may cause discomfort to the user.

Another alternative is provided by the so-called Mitrofanoff principle, by which a suprapubic canal is surgically made by removing parts of a body section, such as the appendix, another part of the intestinal system, eg. a section of the ileum, or any other suitable tubular body tissue, and subsequently attaching one end of the section to the abdominal skin surface whereas the other end penetrates the bladder wall and possibly protrudes into the bladder, the part being attached to the bladder wall at the point of penetration. Obviously, this technique requires surgery under general anaesthetia and implies a loss of bowel or other tissue as well as stitches in the bladder wall.

U.S. Pat. No. 5,704,353 discloses a catheter for temporary placement in the female urethra. The catheter comprises a shaft which in one end has a sealing portion and in the other end a cap. In the lumen of the shaft a one-way valve is enclosed, urine being drained upon activation of the valve by means of a spike. As the length of the shaft has to be adapted to the individual length of the user's urethra and due to the rather elaborate design, this device is expensive and complicated in manufacture. Furthermore, the presence of the sealing portion, which is designed as a mushroom-shaped crown and which in the position of use rests against the inner surface of the bladder, may cause discomfort to the user.

SUMMARY OF THE INVENTION

It is an object of the present invention to provide an access member for use in catheterization of the urinary bladder, which is comfortable to wear and which at the same time provides for an appropriate security against leakage.

It is a further object to provide an access member, by which intermittent catheterization may be performed by a larger group of users and which alleviates the problems encountered in the prior art.

These and other objects are met by an access member adapted to be, in a position of use, accommodated in an artificial or a natural canal in a user, said access member having an outer end and an inner end defining a predetermined length and extending, in the position of use, from the outside of the body of the user through said canal and into the urinary bladder, and comprising at least one wall defining at least one cavity extending substantially throughout said predetermined length, said at least one cavity being intended for intermittently receiving a catheter, said access member being characterized in that said at least one wall of the access member has such a degree of flexibility that said at least one cavity is kept in a substantially closed position by the mutual contact of parts of said at least one wall, but allows for intermittent insertion of a catheter.

The flexibility of the wall or walls of the access member entail that the access member itself is able to provide for the necessary sealing properties, as the access member will inherently have the effect of an automatic non-return valve. In case the access member is exposed to forces in the radial or longitudinal directions, the wall of the access member is pressed against itself or, alternatively, the walls are pressed against each other, thus closing the through-going cavity of the access member between catheterizations, either by a collapse in the radial direction and/or by a bend at the entrance into the bladder. At the inner end of the access member, the cavity is kept closed eg. by contraction of the detrusor and possibly by the pressure exerted by the urine collected in the bladder. By integrating the sealing properties in the access member, it is possible to make the access member according to the invention very comfortable to wear.

During use in connection with suprapubic catheterization, in which the body canal is an artificial canal extending from the user's abdominal wall, contraction of the abdominal muscles keeps the part of the through-going cavity of the access member, which is situated in the region of the abdominal wall, closed, so that urine may not penetrate to the outside and consequently that eg. water may not seep into the bladder when the user is washing or bathing. Nevertheless, intermittent catheterization may be carried out without difficulty by inserting the catheter through the passage provided by the cavity or cavities of the access member.

In relation to the Mitrofanoff principle, the access member according to the invention does not necessarily require surgery under general anaesthetia or any loss of body tissue. By this design an access member is provided which makes intermittent catheterization a feasible and/or attractive alternative to a large number of users which hitherto have been forced to use permanent catheterization. As a consequence, it is possible to reduce the risk of infection in this group of users.

The wall or walls of the access member may comprise a foil or film material, or a foam or a gel. It is likewise possible to form at least a part of the wall or walls of the access member of a net material of eg. metal.

The access member may comprise one wall forming a substantially hose-shaped access member, which provides for a simple manufacture of the access member. The access member may eg. be produced by extrusion or by any other method which provides a preferably seam-less access member.

Alternatively, the access member may comprise at least two walls which are formed by sheets of material having substantially larger dimensions in the longitudinal direction than in the transverse direction and being joined at the respective longitudinally extending edges. By this design, a particularly effective sealing is provided. The sheets may eg. be joined by means of welding, adhesion or any other suitable joining technique.

In order to control the insertion of the access member properly, said sheets may have different thicknesses and different degrees of flexibility. Hereby, it is possible to control the rigidity in the axial direction of the access member.

In an embodiment, which is particularly advantageous with respect to the insertion, at least one blind hole is provided in at least one of said sheets.

In a further embodiment, in which there are at least three sheets and two cavities, and which is particularly advantageous with respect to the insertion as well, one of said cavities is closed at a distance from the outer end of the access member.

In both of these latter embodiments, a suitable fluid, eg. air, may be introduced into the blind hole alternatively the closed cavity, thus increasing the rigidity of the access member in the longitudinal direction thereof during insertion of a catheter whereby the insertion is facilitated.

In an embodiment, which is relatively simple to manufacture and which provides for an easy insertion, the inner end of the access member is designed as a cap having a number of openings.

The access member may furthermore comprise means for securing the outer end of the access member to the abdominal skin surface. Said means may eg. comprise a plate-shaped member, which may be fastened to the skin surface by means of sewing or by adhesion.

In order to provide for additional security against leakage into the access member from the outside, a plug may be provided for introduction into the outer end of said at least one through-going cavity.

In another aspect of the invention, a system for catheterization is provided.

In yet another aspect, a method of replacing an access member is provided. Replacement of the access member may take place by removing the existing access member and shortly after inserting the new access member. If necessary, the new access member may be introduced through the existing one while still in place, whereafter the old one is removed.

BRIEF DESCRIPTION OF THE DRAWINGS

In the following the invention will be described in detail with reference to the schematic drawings, in which FIG. 1 shows a side view of a system according to the invention during catheterization;

FIG. 2 shows a side view of an access member according to the invention in a position of use;

FIG. 3 shows, at a larger scale, a part sectional view of a detail of a system according to another embodiment of the invention;

FIGS. 4 to 8 show, at a larger scale and very schematic, cross-sectional views of different embodiments of an access member according to the invention; and FIG. 9 shows a view corresponding to FIG. 2 of a further embodiment of an access member according to the invention.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In FIGS. 1 and 2 a system for suprapubic catheterization is shown, in which an access member 1 is shown in its position of use in a canal extending from the skin surface 2 of the abdominal wall of the user, which in this case is a female, to the urinary bladder 3, said canal extending above the pubic bone 4. The access member 1 is essentially formed as a hollow tube made from a suitable flexible material. The term "tube" should be interpreted in its broadest sense, ie. as comprising any element having at least one longitudinally extending cavity.

The wall or walls of the access member is/are formed with a small thickness, which in this respect means that the thickness should be sufficiently low so as to be able to allow parts of one wall, or different walls to contact each other. A preferred thickness depends on the material chosen.

Examples of suitable materials are eg. film or foil made from polyethylene, polyurethane, poly-propylene or like material, a flexible foam made from any suitable material, artificial blood vessels, pig guts, Tripsin, a gel, such as a hydrogel or a silicone gel which are widely used for eg. implants or any other gel, or any other material which can meet the demands to the access member, both with respect to physical properties and bio-compatibility. In addition to being flexible and being able to be produced in a small thickness, the material should thus preferably be soft, possess low surface friction, be able to be coated, welded, heat-sealed and/or glued, adhered or joined using any other suitable joining technique and be hydrophobic. Furthermore, the material should be able to collapse in a radial direction but preferably be stable axially, and could for insertion purposes be rolled up. With respect to the bio-compatibility of the material, it should prevent stenosis, encrustation and bio-film formation, not form in-growth with tissue and be non-toxic.

Parts of the access member may comprise different materials. For instance, the part situated in the region of the abdominal wall could be designed of a net material of for example, metal.

In order to prevent or reduce even further these unwanted effects, the access member may be provided with a coating on the outer side and/or the inner side. The coating may eg. contain antibacterial agents or disinfectants known per se, such as metal ions, halogen ions, antibiotics or sulpha. It is also possible that the wall or walls of the access member may have properties allowing slow release of any known antibacterial or disinfective substances.

The access member 1 has an outer end 1a which may be secured to the skin surface 2 by any suitable means, eg. a medical grade adhesive, and an inner end 1b which protrudes well into the bladder 3, the outer and inner ends 1a, 1b defining a predetermined length. Examples of suitable adhesives are adhesives based on styrene-isoprene-styrene block polymer (SIS), polyisobutylene (PIB), Silicone Tacky Gel, polyvinylether (PVE) and acrylic polymers. In the embodiment shown, the cavity in the access member 1 extends throughout the predetermined length such that a catheter 5 may be inserted through the canal provided by the access member 1 in order to attain the catheterization position as shown in FIG. 1, in which urine flows from the bladder 3 through inlet openings 5a provided at the end of the catheter and out to a suitable draining means (not shown).

After catheterization, the catheter 5 is retracted from the bladder 3 through the access member 1 which remains seated in the body of the user.

As indicated in FIG. 2 the access member 1 assumes, at least partially, a flattened position between catheterizations as a result of the involuntary contraction of the detrusor and abdominal muscles, and of the pressure exerted by the urine collected in the bladder, respectively. Consequently, the passage between the bladder 3 and the outside of the body provided by the cavity in the access member is kept closed such that virtually no urine may penetrate to the outside. Moreover, the closure of the canal implies that liquid such as water will not seep into the bladder when the user for example washes, takes a shower or bathes.

Initial positioning of the access member 1 may take place by first penetrating the abdominal wall and the wall of the bladder 3 by means of a trocar and by subsequently inserting a catheter or other applicator means carrying on its outer or inner side the access member 1.

In order to insert the access member 1 without discomfort to the user, the exterior surface of the access member may be provided with a coating to provide a slippery low-friction surface character. In order to retain the access member safely within the body the coating may be of a temporary character such that the exterior surface after a predetermined period of time looses its low-friction character.

Alternatively, application of the access member may take place as shown in FIG. 3, showing a part of an embodiment of the inventive system comprising a catheter 25 and an access member 21. In this embodiment, an inner end 21b of the access member 21 adapted to be positioned at the end of the catheter 25 provided with urine inlet openings 25a is designed as a cap having openings 21c which allow urine to flow into the catheter 25 through the inlet openings 25a.

In the following, different designs of the access member will be described with reference to FIGS. 4 to 8. In these very schematic cross-sectional views, certain details of the access member may be omitted, ie. the access member may comprise parts not indicated in theses Figures.

In its most simplified form as shown in FIG. 4, the access member 41 comprises only one circumferential wall 42 which defines a cavity 45 for receiving a catheter during catheterization, thus providing the access member 41 with a substantially hose-shaped appearance. It should be noted that the access member 41 is shown in an open or catheter-receiving position, and it is to be understood that the cavity 45 is kept closed between catheterizations as parts of the wall 42 are pressed against each other.

In the FIG. 5 embodiment, the access member 51 comprises two walls which are formed by sheets 52,53 of material having substantially larger dimensions in the longitudinal direction than in the transverse direction and being joined at the respective longitudinally extending edges. The cavity 55 defined by the sheets 52,53 is shown in a slightly open position for reasons of clarity only. In one sheet 53, a blind hole 54 is provided in any suitable manner. During insertion of the access member 51 into the canal, a suitable fluid, eg. air, is introduced into the blind hole 54. As long as the fluid is present in the hole 54, the rigidity of the access member in the longitudinal direction thereof is increased, and the insertion of the access member 51 into the canal is eased.

A similar principle is shown in FIG. 6, in which the access member 61 comprises three walls likewise formed by sheets 62,63,64 of any suitable material, of which sheets 62 and 63 define the catheter receiving cavity 65. The cavity 66 defined between sheets 64 and 63 is closed at a distance from the outer end of the access member, and eg. air may be introduced into the closed cavity 66 in order to ease insertion of the access member 61.

In the FIG. 7 embodiment, the sheets 72,73 forming the walls of the access member 71 have different thicknesses and may in addition thereto have different degrees of flexibility. In this manner secure closing of the cavity as well as an eased introduction is ensured. In addition or alternatively, the thickness and/or the degree of flexibility may vary in the circumferential direction of the access member.

In the embodiment shown in FIG. 8 the cavity 85 defined by the sheets 82,83 forming the walls of the access member 81 is filled with a gel 86, which functions partly as a lubricant during insertion of the catheter, partly as an additional security against leakage.

In FIG. 9 an access member 91 which may be of any of the types described in the above is at its outer end 91a fastened to a plate-shaped member 93, eg. by means of a layer of adhesive 92 or in any other way, such as eg. by forming the plate-shaped member 93 integrally with the access member 91. The plate-shaped member 93 is in turn fastened to the abdominal skin surface by means of eg. a layer 94 of medical grade adhesive. A plug member 95 which is intended to be inserted into the outer end 91a of the access member 91 provides for increased safety against in-seeping of eg. water into the access member 91. The plug member 95 may be coated as described in the above in connection with the coating of the access member itself.

The access member and the system according to the invention may alternatively be used in urethral catheterization. By using an access member in connection with urethral catheterization, self-catheterization may be performed even by users having a reduced dexterity and mobility as an access member facilitates the operation of finding the urethral orifice, especially in women. In contrast to permanent catheterization the muscles are furthermore allowed to contract and relax. By letting the outer end protrude from the urethral orifice, this end may easily be gripped by the user in order to position the catheter correctly. This operation is thus much facilitated in relation to urethral catheterization without an access member and makes it possible for even eg. sclerosis patients to perform intermittent self-catheterization which in turn implies that this group of patients gains a significantly improved quality of life in relation to use of permanent catheterization.

The access member or system may likewise be used for introduction of eg. pharmaceuticals into the urinary bladder or for washing/rinsing the bladder.

The invention is not limited to the embodiments shown and described in the above. Several modifications and combinations of the embodiments shown and described are conceivable within the scope of the appended claims.

What is claimed is:

1. An access member adapted to be, in a position of use, accommodated in an artificial or a natural canal in a user, said access member comprising an outer end and an inner end defining a predetermined length, said length extending, in the position of use, from outside of a body of the user through said canal and into the user's urinary bladder, at least one wall defining at least one cavity extending substantially throughout said predetermined length, said at least one wall of the access member allowing for intermittent insertion of a catheter within said cavity while having a degree of flexibility such that, when a catheter is not inserted, said at least one cavity is kept in a substantially closed position by the mutual contact of parts of said at least one wall.

2. The access member according to claim 1, wherein the wall or of the access member includes a foil or film material.

3. The access member according to claim 1, wherein the wall of the access member includes a foam or a gel.

4. The access member according to claim 1, wherein at least one part of the wall of the access member includes a net material made of metal.

5. The access member according to claim 1, wherein one wall forms a substantially hose-shaped access member.

6. The access member according to claim 1, wherein at least two walls are formed by sheets of material having substantially larger dimensions in the longitudinal direction than in the transverse direction and joined at the respective longitudinally extending edges.

7. The access member according to claim 6, wherein said sheets are joined by means of welding, adhesion or any other suitable joining technique.

8. The access member according to claim 6, wherein said sheets have different thicknesses.

9. The access member according to claim 6, wherein said sheets have different degrees of flexibility.

10. The access member according to claim 6, wherein at least one blind hole is provided in at least one of said sheets.

11. The access member according to claim 6, and having at least three sheets and two cavities, wherein one of said cavities is closed at a distance from the outer end of the access member.

12. The access member according to claim 1, wherein the inner end of the access member is designed as a cap having a number of openings.

13. The access member according to claim 1, further comprising means for securing the outer end of the access member to the abdominal skin surface.

14. The access member according to claim 13, wherein said means includes a plate-shaped member.

15. The access member according to claim 13, wherein the plate-shaped member is fastened to the skin surface by means of an adhesive.

16. The access member according to claim 1, wherein a plug member is provided for insertion into the outer end of said at least one through-going cavity.

17. A system for catheterization of the urinary bladder through an artificial or a natural canal in a user, comprising a catheter adapted to be inserted through the canal, and an access member having an outer end and an inner end defining a predetermined length, said length extending, in the position of use, from outside of a body of the user through said canal and into the user's urinary bladder, at least one wall defining at least one cavity extending substantially throughout said predetermined length, said at least one wall of the access member allowing for intermittent insertion of the catheter within said cavity while having a degree of flexibility such that, when the catheter is not inserted, said at least one cavity is kept in a substantially closed position by the mutual contact of parts of said at least one wall.

18. A method of replacing an access member having an outer end and an inner end defining a predetermined length, said length extending, in the position of use, from the outside of the body of the user through an artificial or a natural canal in a user and into the urinary bladder, at least one wall defining at least one cavity extending substantially throughout said predetermined length, said at least one wall of the access member allowing for intermittent insertion of a catheter within said cavity while having a degree of flexibility such that, when a catheter is not inserted, said at least one cavity is kept in a substantially closed position by the mutual contact of parts of said at least one wall, comprising the steps of removing a first access member positioned in said canal and inserting a second, substitute access member.

19. The method according to claim 18, wherein said step of removing is performed before said step of inserting the second access member.

20. The method according to claim 18, wherein said step of inserting includes introducing said substitute access member through the first access member positioned in said canal and said step of removing the first access member is performed thereafter.

* * * * *